(12) United States Patent
Casas et al.

(10) Patent No.: US 11,311,711 B2
(45) Date of Patent: Apr. 26, 2022

(54) AXIAL BLOOD PUMP WITH IMPELLER RINSE OPERATION

(71) Applicant: HeartWare, Inc., Miami Lakes, FL (US)

(72) Inventors: Fernando Casas, Miami Lakes, FL (US); Carlos Reyes, Davie, FL (US); Justin Wolman, Aventura, FL (US); Thomas R. Johnson, Franklin, MA (US)

(73) Assignee: HeartWare, Inc., Miami Lakes, FL (US)

( * ) Notice: Subject to any disclaimer, the term of this patent is extended or adjusted under 35 U.S.C. 154(b) by 186 days.

(21) Appl. No.: 16/260,648

(22) Filed: Jan. 29, 2019

(65) Prior Publication Data

US 2019/0231952 A1    Aug. 1, 2019

Related U.S. Application Data

(60) Provisional application No. 62/624,255, filed on Jan. 31, 2018.

(51) Int. Cl.
| | |
|---|---|
| *A61M 60/40* | (2021.01) |
| *A61M 60/50* | (2021.01) |
| *A61M 60/148* | (2021.01) |
| *A61M 60/205* | (2021.01) |

(52) U.S. Cl.
CPC .......... *A61M 60/40* (2021.01); *A61M 60/148* (2021.01); *A61M 60/205* (2021.01); *A61M 60/50* (2021.01); *A61M 2205/50* (2013.01)

(58) Field of Classification Search
USPC ......................................................... 600/16
See application file for complete search history.

(56) References Cited

U.S. PATENT DOCUMENTS

| | | | |
|---|---|---|---|
| 5,385,581 | A | 1/1995 | Bramm et al. |
| 5,928,131 | A | 7/1999 | Prem |
| 6,302,661 | B1 | 10/2001 | Khanwilkar et al. |
| 6,595,762 | B2 | 7/2003 | Khanwilkar et al. |
| 8,007,254 | B2 | 8/2011 | LaRose et al. |

(Continued)

FOREIGN PATENT DOCUMENTS

| | | |
|---|---|---|
| EP | 1481699 A1 | 12/2004 |
| WO | 2008106103 A2 | 9/2008 |

(Continued)

OTHER PUBLICATIONS

International Search Report and Written Opinion dated May 6, 2019, for corresponding International Application No. PCT/US2019/015561; International Filing Date: Jan. 29, 2019 consisting of 10 pages.

*Primary Examiner* — Nicole F Lavert
(74) *Attorney, Agent, or Firm* — Shumaker & Sieffert, P.A.

(57) ABSTRACT

A method of controlling a blood pump including executing a control command to temporarily displace an impeller of the blood pump within a pump housing from a first axial position relative to the pump housing to a second axial position a distance away from the first axial position using a vector control method, and causing the impeller to move from the second axial position to a third axial position, the third axial position including a positive and a negative displacement of the impeller relative to the first axial position.

17 Claims, 9 Drawing Sheets

(56) References Cited

U.S. PATENT DOCUMENTS

| | | |
|---|---|---|
| 8,636,638 B2 | 1/2014 | Timms |
| 9,427,508 B2 | 8/2016 | Reyes et al. |
| 9,492,601 B2 | 11/2016 | Casas et al. |
| 9,511,179 B2 | 12/2016 | Casas et al. |
| 9,561,313 B2 | 2/2017 | Taskin |
| 10,426,879 B2 | 10/2019 | Farnan |
| 10,660,998 B2 | 5/2020 | Hodges |
| 10,732,583 B2 | 8/2020 | Rudser |
| 11,131,968 B2 | 9/2021 | Rudser |
| 11,185,682 B2 | 11/2021 | Farnan |
| 2002/0094281 A1 | 7/2002 | Khanwilkar et al. |
| 2003/0163019 A1 | 8/2003 | Goldowsky |
| 2005/0025630 A1 | 2/2005 | Ayre |
| 2007/0253842 A1 | 11/2007 | Horvath et al. |
| 2009/0067989 A1* | 3/2009 | Estes ............... A61M 5/14244 415/118 |
| 2012/0245680 A1* | 9/2012 | Masuzawa ............ F04D 29/042 623/3.11 |
| 2012/0245681 A1 | 9/2012 | Casas et al. |
| 2014/0066691 A1 | 3/2014 | Siebenhaar |
| 2014/0100413 A1 | 4/2014 | Casas et al. |
| 2014/0288352 A1 | 9/2014 | Yanai |
| 2014/0357937 A1 | 12/2014 | Reyes et al. |
| 2016/0166211 A1 | 6/2016 | Brown et al. |
| 2016/0235898 A1 | 8/2016 | Yanai et al. |
| 2017/0165407 A1 | 6/2017 | Farnan |
| 2017/0185054 A1 | 6/2017 | Rudser |
| 2017/0340788 A1* | 11/2017 | Korakianitis ....... A61M 60/857 |
| 2018/0085507 A1 | 3/2018 | Casas et al. |
| 2019/0231952 A1 | 8/2019 | Casa |
| 2019/0343999 A1 | 11/2019 | Wolman et al. |
| 2019/0351118 A1 | 11/2019 | Graichen et al. |

FOREIGN PATENT DOCUMENTS

| | | |
|---|---|---|
| WO | 2010118476 A1 | 10/2010 |
| WO | 2016130944 A1 | 8/2016 |
| WO | 2016187057 A1 | 11/2016 |
| WO | 2017032751 A1 | 3/2017 |
| WO | 2017120453 A1 | 7/2017 |

* cited by examiner

AXIAL BLOOD PUMP WITH IMPELLER RINSE OPERATION

CROSS-REFERENCE TO RELATED APPLICATION

This application claims the benefit of U.S. Application Ser. No. 62/624,255, filed Jan. 31, 2018.

FIELD

The present technology is generally related to blood pumps, and more particularly, to a method of controlling an axial motion of an impeller within a blood pump.

BACKGROUND

Mechanical Circulatory Support Devices ("MCSDs"), such as ventricular assist devices, are commonly used to assist the pumping action of a failing heart. Typically, an MCSD includes an implantable blood pump that is surgically implanted in a patient's body. More specifically, the MCSD includes a housing with an inlet, an outlet, and a rotor mounted therein. The inlet is connected to a chamber of the patient's heart, typically the left ventricle, whereas the outlet is connected to an artery, such as the aorta. Rotation of the rotor drives blood from the inlet towards the outlet and thus assists blood flow from the chamber of the heart into the artery. One exemplary MCSD is the MVAD® pump.

Blood pumps used in MCSDs are desirably provided with contactless bearings so that the rotor floats within the housing in operation. With contactless bearings, there is no solid-to-solid contact between the rotor and the housing, and thus no mechanical wear during operation. One form of contactless bearing is a hydrodynamic bearing. In a hydrodynamic bearing, the liquid being pumped passes between a surface of the rotor and the surfaces of a hydrodynamic bearing which creates a clearance that is many times larger than the dimensions of blood cells. The surfaces are configured so that as the rotor turns, the fluid disposed between these surfaces exerts pressure on the surface of the rotor that holds the rotor away from the housing. However, in some cases the blood passing through the blood pump may contain particles that lead to thrombus, a solid or semi-solid deposit generated within a patient's body, if not removed. The thrombus can lodge on the surface of the hydrodynamic bearing and impede its operation, which is hazardous or lethal for the patient. Unfortunately, known blood pumps fail to include a system for dislodging and/or removing the particles from the blood pump.

SUMMARY

The techniques of this disclosure generally relate to systems and methods of controlling an axial motion of an impeller within a blood pump.

In one aspect, the present disclosure provides a method of controlling a blood pump including executing a control command to temporarily displace an impeller of the blood pump within a pump housing from a first axial position relative to the pump housing to a second axial position a distance away from the first axial position using a vector control method; and causing the impeller to move from the second axial position to a third axial position, the third axial position including a positive and a negative displacement of the impeller relative to the first axial position.

In another aspect, the positive and the negative displacement of the impeller defines an oscillating motion.

In another aspect, the disclosure provides the method including dislodging a foreign particle from the pump housing when the foreign particle is proximate the impeller and the impeller is in the third axial position.

In another aspect, a hydraulic and magnetic suspension system of the blood pump causes the positive and a negative displacement of the impeller.

In another aspect, the disclosure provides the distance of the first axial position relative to the pump housing corresponding to a thrust produced by the impeller.

In another aspect, the disclosure provides the method including controlling the movement of the impeller from the second axial position to the third axial position.

In another aspect, the disclosure provides the method including executing a second control command to temporarily displace the impeller from the first axial position to a fourth axial position a distance away from the first axial position using the vector control method and causing the impeller to move from the fourth axial position to a fifth axial position, the fifth axial position including a positive and a negative displacement of the impeller relative to the first axial position.

In another aspect, the vector control method is a three-phase sensorless field-oriented control method including a set of three stator windings and a set of three alternating currents.

In another aspect, the disclosure provides the method including executing the control command when the first axial position of the impeller is within a normal operating region, and the normal operating region is closer in proximity to an outlet of the pump housing than an inlet of the pump housing.

In another aspect, the disclosure provides the second axial position being within a displacement region, and the displacement region is in a direction toward the inlet of the pump housing.

In one aspect, the present disclosure provides a method of controlling a blood pump including detecting a presence of a foreign particle within a pump housing proximate an impeller of the blood pump when the impeller is in a first axial position relative to the pump housing, the first axial position including the impeller being closer in proximity to an outlet of the blood pump than an inlet of the blood pump; executing a control command to temporarily displace the impeller from the first axial position to a second axial position using a vector control method, the second axial position being in a direction toward the inlet of the blood pump; and causing the impeller to move from the second axial position to a third axial position, the third axial position including a positive and a negative displacement of the impeller relative to the first axial position.

In another aspect, the disclosure provides the positive and the negative displacement of the impeller defining an oscillating motion configured to displace the foreign particle in a direction toward an outlet of the pump housing.

In another aspect, a hydraulic and magnetic suspension system of the blood pump causes the positive and a negative displacement of the impeller and the displacement of the impeller from the first axial position relative to the pump housing corresponds to a thrust produced by the impeller.

In another aspect, the disclosure provides the method including executing a second control command within a select time period following the control command to temporarily displace the impeller from the first axial position to a fourth axial position a distance away from the first axial position using the vector control method.

In another aspect, the disclosure provides the method including causing the impeller to move from the fourth axial position to a fifth axial position, the fifth axial position including a positive and a negative displacement of the impeller relative to the first axial position.

In another aspect, the displacement of the impeller from the first axial position to the second axial position includes the impeller traveling along a trajectory path at least partially defined by an axial stiffness of the blood pump.

In one aspect, the present disclosure provides a system for controlling a blood pump including a control circuit for communicating with the blood pump, the control circuit including control circuitry configured to execute a control command to temporarily displace an impeller of the blood pump within a pump housing from a first axial position relative to the pump housing to a second axial position a distance away from the first axial position using a vector control method; and cause the impeller to move from the second axial position to a third axial position, the third axial position including a positive and a negative displacement of the impeller relative to the first axial position.

In another aspect, the disclosure provides the positive and the negative displacement of the impeller defining an oscillating motion.

In another aspect, the disclosure provides the distance of the first axial position relative to the pump housing corresponding to a thrust produced by the impeller.

In another aspect, the disclosure provides the system including the vector control method being a three-phase sensorless field-oriented control method including a set of three stator windings and a set of three alternating currents.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
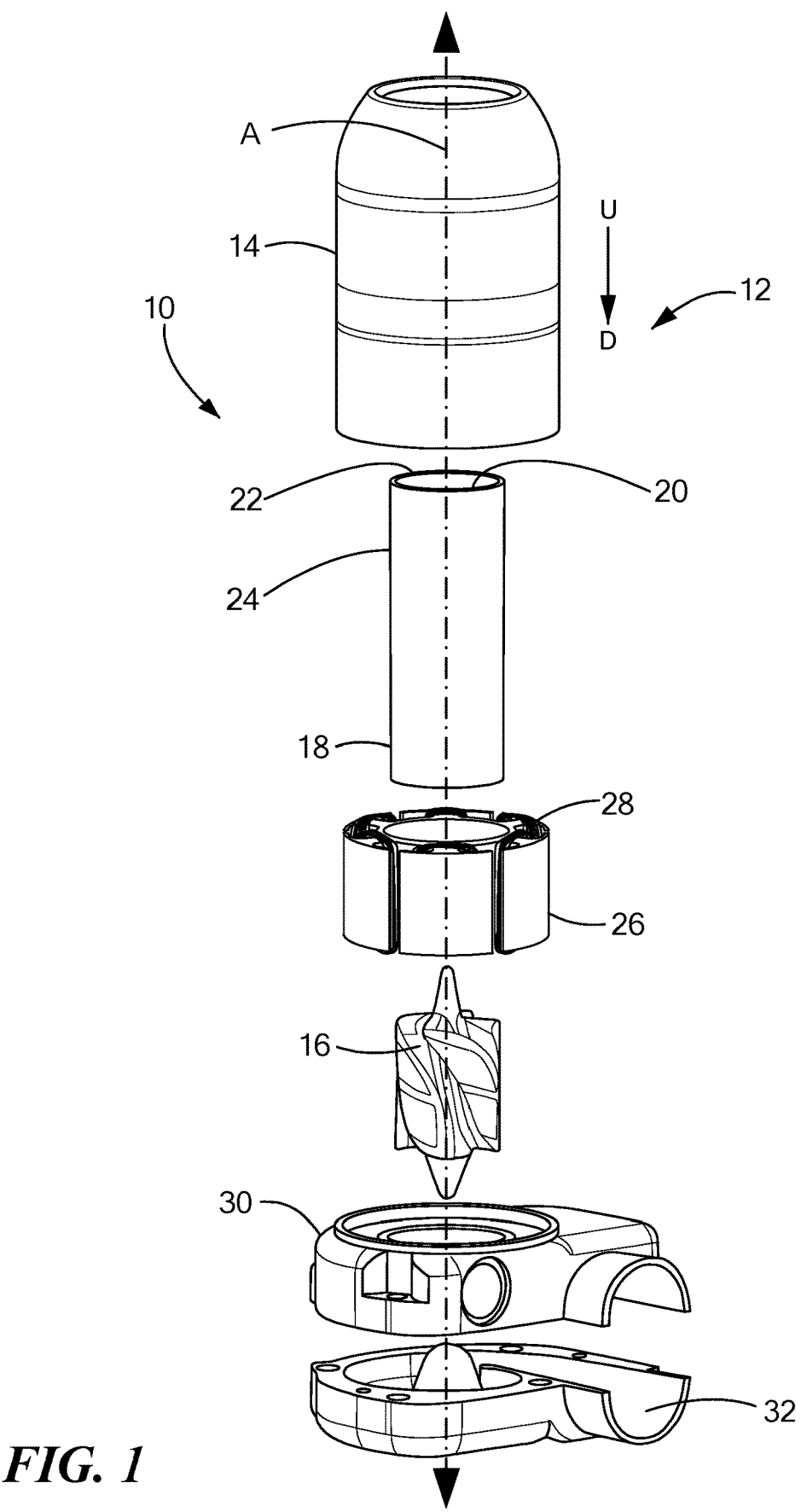
FIG. 1 is an exploded view that illustrates a blood pump including a pump housing having an impeller therein.

Before describing in detail exemplary embodiments, it is noted that the claims reside primarily in combinations of system components and processing steps related to a method of controlling a blood pump. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Referring now to the drawings in which like reference designators refer to like elements there is shown in FIG. 1 an exemplary implantable blood pump constructed in accordance with the principles of the present application and designated generally "10." The blood pump 10 may be an axial flow blood pump such as, without limitation, the MVAD® pump. Further details associated with rotary blood pumps are discussed in U.S. Pat. Nos. 8,007,254 and 9,561,313, the disclosures of which are hereby incorporated in the entirety. The blood pump 10 includes a housing having an impeller, the axial position of which may be controlled using one or more methods described herein so as to execute an oscillating motion to wash the impeller, thereby dislodging foreign particles, such as thrombus, when present within the blood pump 10.

The blood pump 10 includes a pump housing 12 having an inlet cannula 14 and an impeller 16 to impel the blood. The inlet cannula 14 may include an inner tube 18 formed from a non-magnetic material, such as a ceramic. The inner tube 18 includes an interior surface 20 defining a cylindrical bore 22 for receiving the impeller 16 therein. The inner tube 18 may also include a cylindrical outer surface 24 configured to be surrounded by a stator 26 having one or more coils 28. A voltage is applied to the coils 28 to produce an electromagnetic force to rotate the impeller 16, thus impelling the blood along a flow path through the blood pump 10 from an upstream direction "U" to a downstream direction "D".

The housing defines a pump axis "A" extending from the inlet cannula 14 through a lower housing portion 30 having an outlet 32 that is proximate a volute. The impeller 16 moves in an axial direction relative to the housing 12 along the pump axis A. During rotation, the impeller 16 is levitated within the housing 12 by contactless bearings, such as magnetic bearings, hydrodynamic bearings or a combination of the two which produce a hydraulic and magnetic suspension system. For example, with reference to FIGS. 1 and 2, the pump may include a sensorless three-phase brushless direct-current (BLDC) motor 34 with the stator 26 having three windings controlled by a different respective phase U, V, W, of a power input for three-phase motor control. The BLDC motor includes an inverter circuit to convert a DC input to the three-phase output. Alternatively, the blood pump 10 may receive an alternating current (AC) three-phase input.

Figure 2:
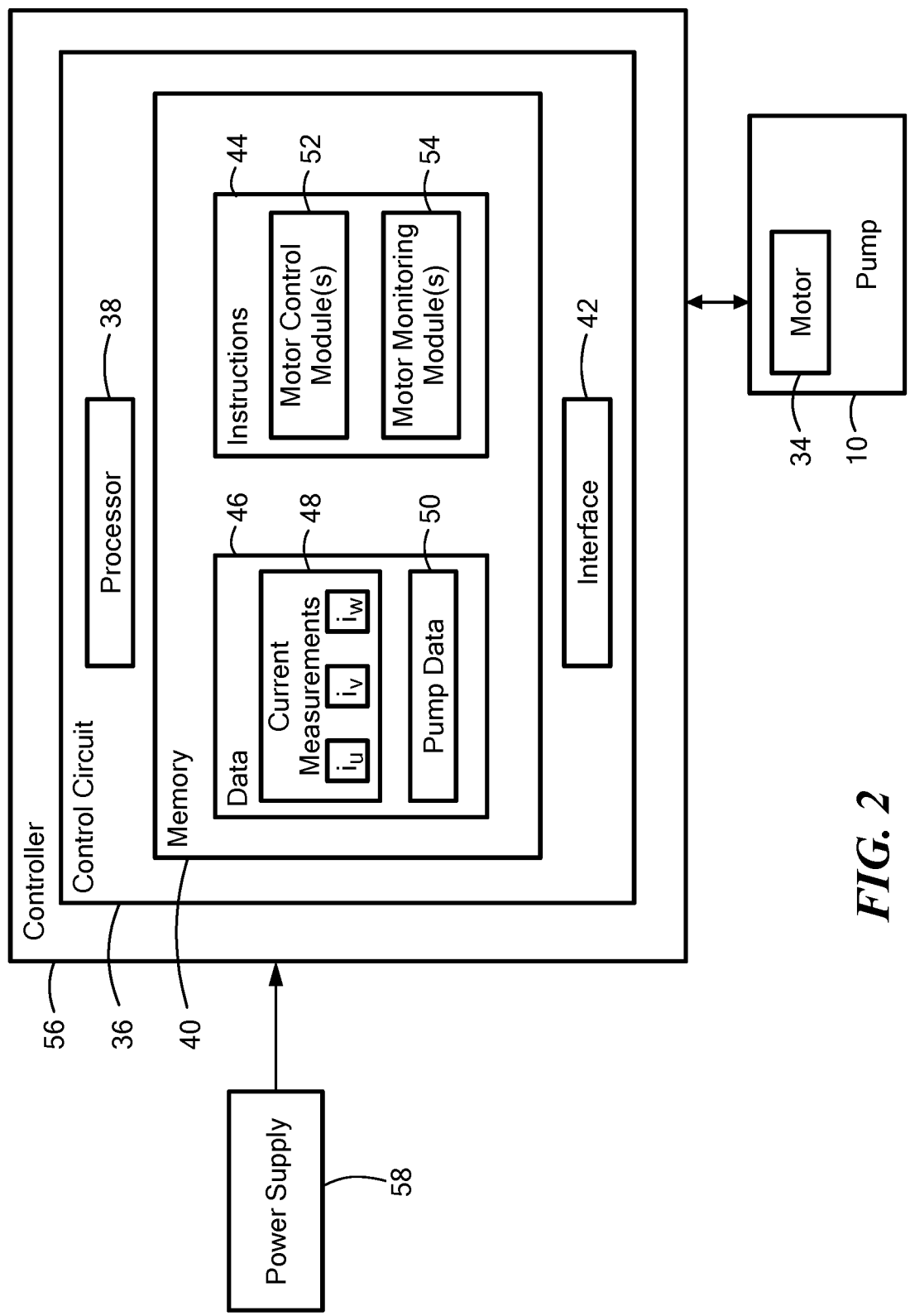
FIG. 2 is block diagram that illustrates an exemplary pump system including the blood pump of FIG. 1 and a control circuit in communication with the blood pump.

FIG. 2 is a block diagram that illustrates an example control circuit 36 having control circuitry for monitoring and controlling startup and subsequent operation of the motor 34, including executing a three-phase sensorless field-oriented control (FOC) method. Exemplary FOC methods are disclosed in commonly owned and co-pending U.S. patent application Ser. No. 15/710,323, which is incorporated herein in the entirety. The control circuit 36 is coupled to the motor 34 to control operation of the motor 34, such as through one or more implanted cables. The control circuit 36 includes a processor 38 having processing circuitry, a memory 40, and an interface 42 for interfacing with the motor 34. The memory 40 stores information accessible by the processor 38, including instructions 44 that may be executed by the processor 38. The memory 40 also includes data 46 that may be retrieved, manipulated or stored by the processor 38. The memory 40 is of a type capable of storing information accessible by the processor 38, such as a hard-drive, memory card, ROM, RAM, DVD, CD-ROM, write-capable, and read only memories. The processor 38 may be a type of well-known processor, such as a commercially available processor. Alternatively, the processor 38 may be a dedicated controller such as an ASIC.

The data 46 may be retrieved, stored or modified by the processor 38 in accordance with the instructions 44. The data may also be formatted in any computer-readable format such as, but not limited to, binary values, ASCII or Unicode. Moreover, the data 46 may comprise any information sufficient to identify the relevant information, such as numbers, descriptive text, proprietary codes, pointers, references to data stored in other memories (including other network locations) or information that is used by a function to calculate the relevant data.

The control circuit 36 includes hardware and software for controlling the various aspects of the operation of the motor 34. The control circuit 36 is coupled to the motor 34 through the interface 42 to collect at least some of data 46 from the motor 34. For example, the data 46 may include one or more electrical current measurements 48 of the motor windings of the stator 26 (FIG. 1). The current measurements may be provided from current sensors, such as first, second and third shunts R1, R2, R3 for measuring the respective currents $i_u$, $i_v$, $i_w$ of the motor windings. In one example, each of the shunts may be connected to a respective amplifier or programmable gain amplifier (PGA), to amplify the measured voltage across the shunt. Given the known resistance of each shunt, the amplified voltages may be converted back into current measurements. An analog to digital (A/D) converter may also be included for receiving the amplified voltages and converting them into corresponding digital signals to be received by the control circuit 36. The data 46 may include pump data 50, such as flow rate of blood exiting the pump, flow pulsatility, differential pressure across the pump, motor speed, current supplied to the motor, and the like.

The instructions 44 stored in the memory 40 may include one or more instruction sets or modules, for performing certain operations in accordance with the present disclosure. One such module may be a motor control module 52 for controlling operation of the motor 34 (e.g., increasing or decreasing current supplied to the motor), such as in accordance with the FOC routines described herein. The instructions may also include one or more motor monitor modules 54 for monitoring operation of the motor 34. Examples of motor control and monitoring modules may be found in the commonly owned and copending U.S. patent application Ser. Nos. 13/355,297, 13/951,302, 14/294,448, 14/950,467, 62/266,871 and 62/271,618, the disclosures of which are incorporated herein by reference in their entireties. The control circuit 36 may be disposed within a controller 56 which is connected to a power supply 58.

Figure 3:
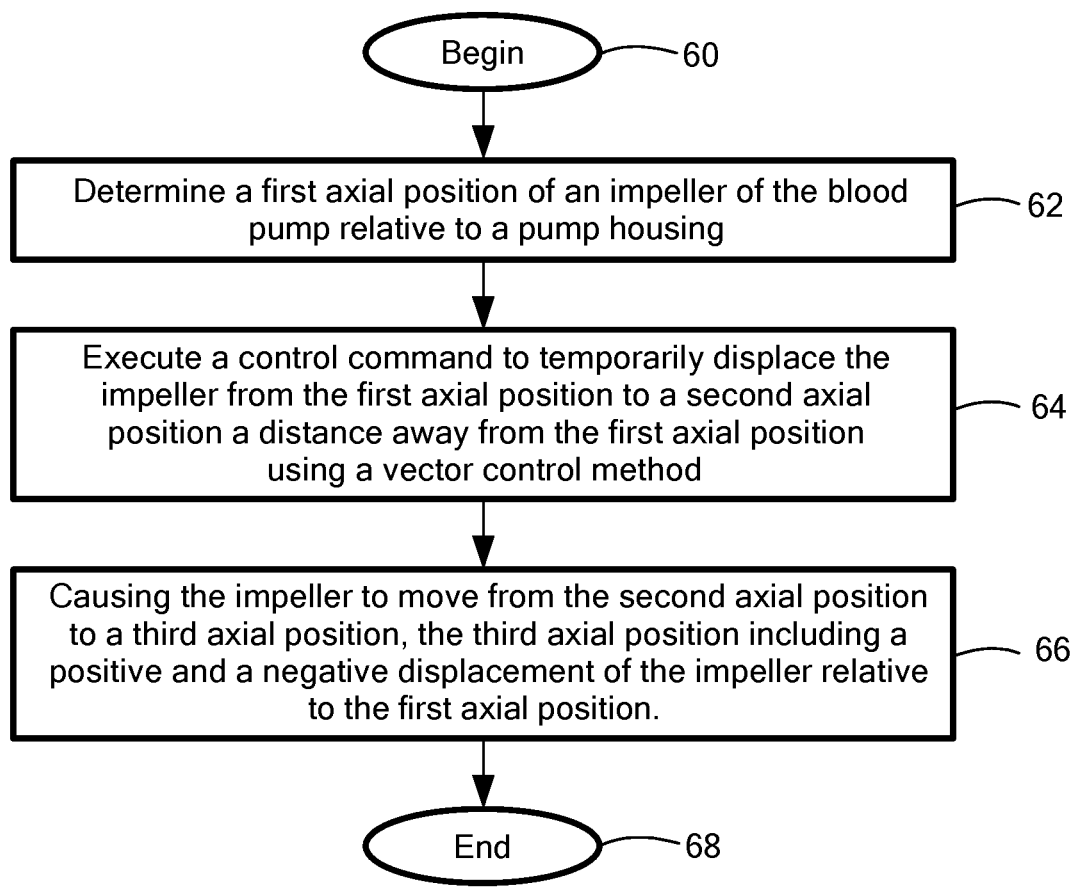
FIG. 3 is a flow chart that illustrates a method of controlling an axial motion of the impeller of the blood pump of FIG. 1.

FIG. 3 is a flow chart that illustrates exemplary process steps for implementing a method of controlling the axial position or motion of the impeller 16 within the blood pump 10. The order of the process steps may vary and one or more process steps may be added and/or omitted. FIG. 3 may be viewed with FIG. 4 which is a perspective view of the blood pump 10 being assembled, i.e., in an assembled configuration, and FIG. 5 which is a cross-sectional perspective view of the blood pump 10 taken along section A-A of FIG. 4.

The method begins with step 60 and proceeds to step 62 including determining a first axial position 70 of the impeller 16 relative to the housing 12. The first axial position 70 may be determined when the impeller 16 is in a normal operating state, such as on a routine daily basis, or when the impeller 16 is at rest. The first axial position 70 is within a normal operating region 72 along the pump axis A that generally includes the impeller 16 being closer in proximity to an outlet channel 74 defined by the outlet 32 than a stop member 76 which is proximate an inlet 78 of the inlet cannula 14. When operating, the first axial position 70 corresponds to a thrust produced by the impeller 16. For example, when fluid, such as blood, passes through the blood pump 10, the fluid imparts a thrust on the impeller 16 which causes the impeller 16 to move. A magnitude of the thrust is related to a fluid flow rate through the blood pump 10. In other words, the axial position of the impeller 16 relative to the housing 12 is proportional to the fluid flow rate through the blood pump 10, which is proportional to the thrust.

Figure 4:
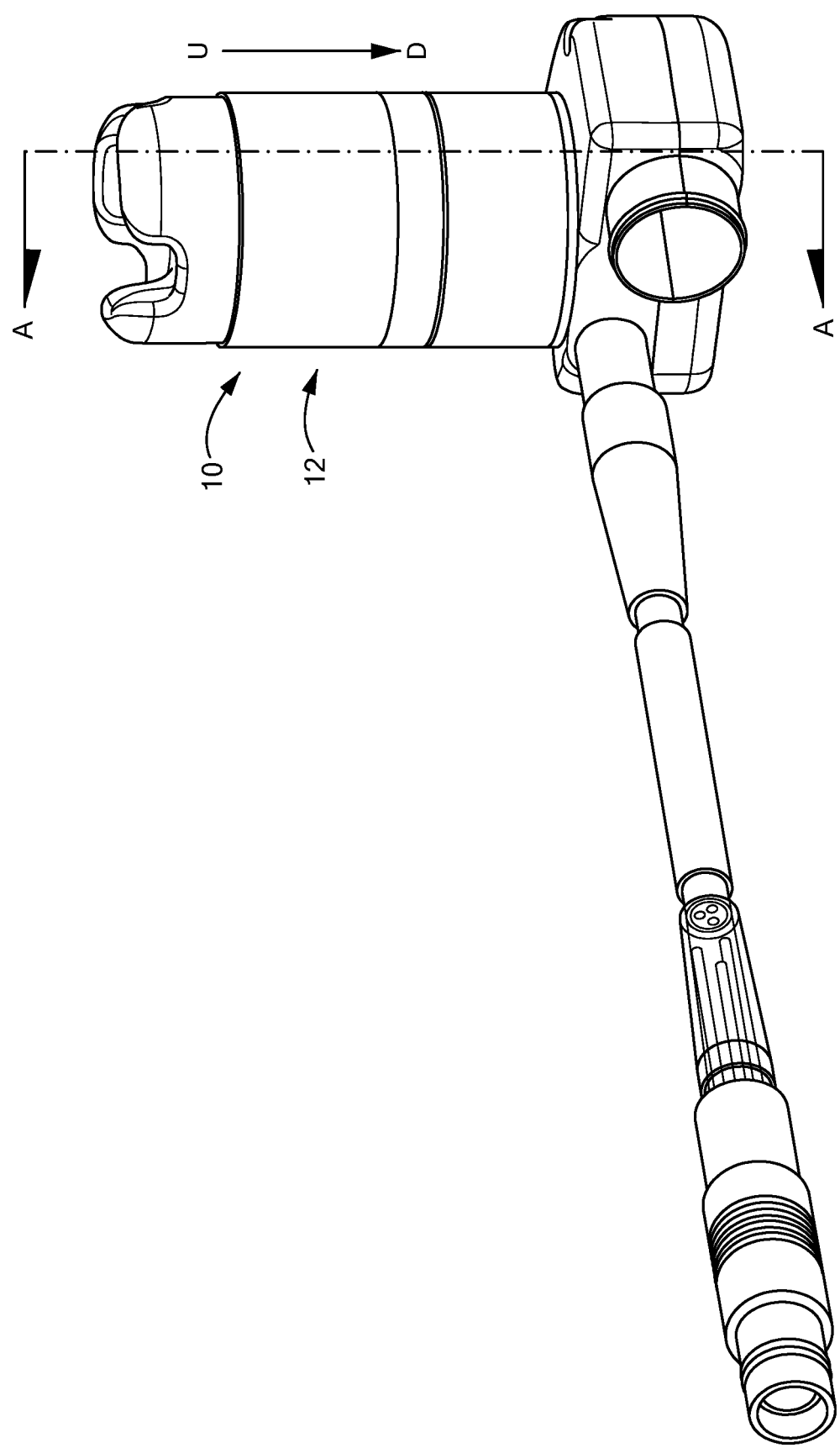
FIG. 4 is a perspective view that illustrates the blood pump of FIG. 1.
Figure 5:
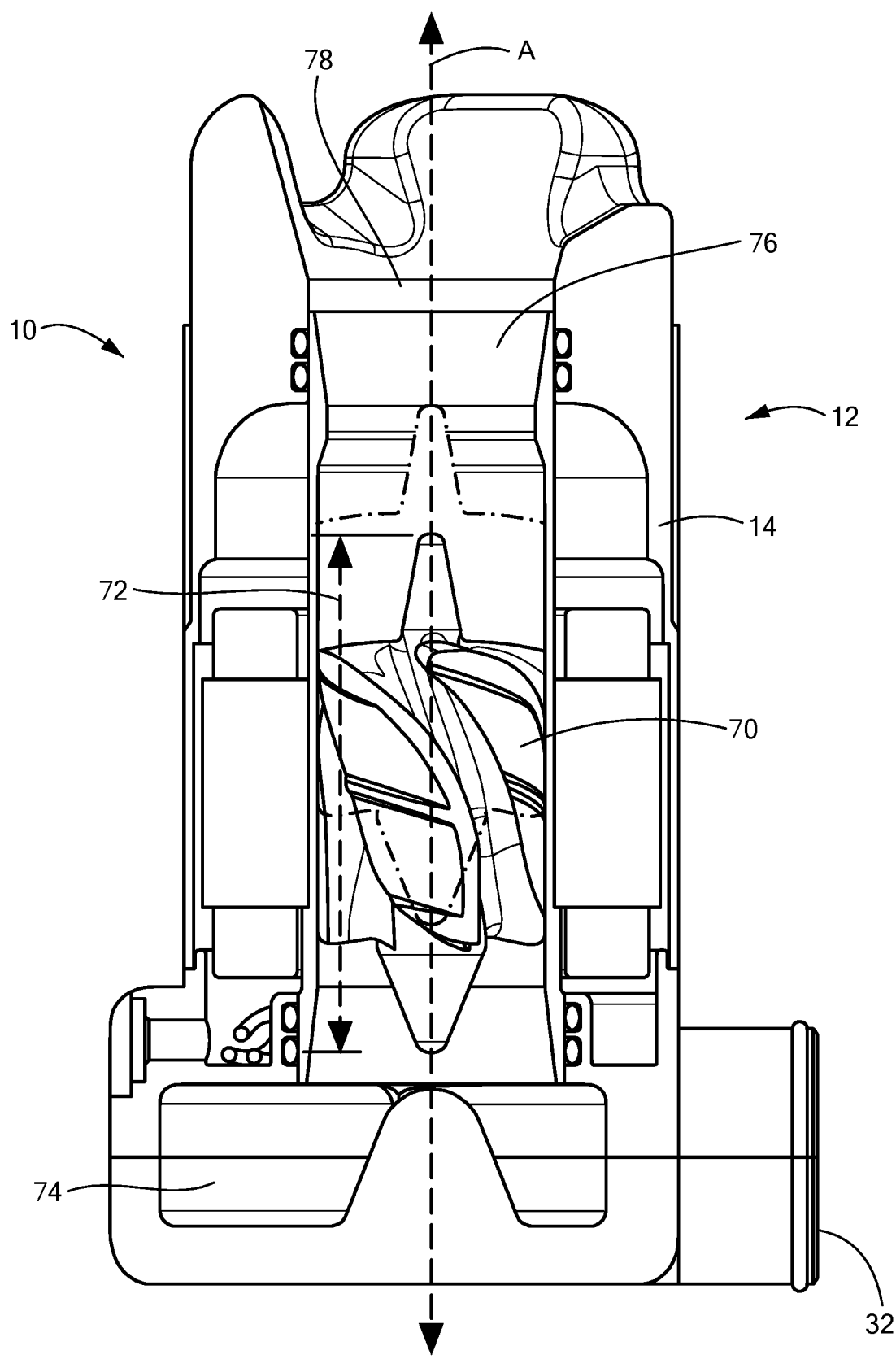
FIG. 5 is a cross-sectional view that illustrates the blood pump of FIG. 1 taken along section A-A of FIG. 4 and including the impeller being in a first axial position relative to the pump housing.
Figure 6:
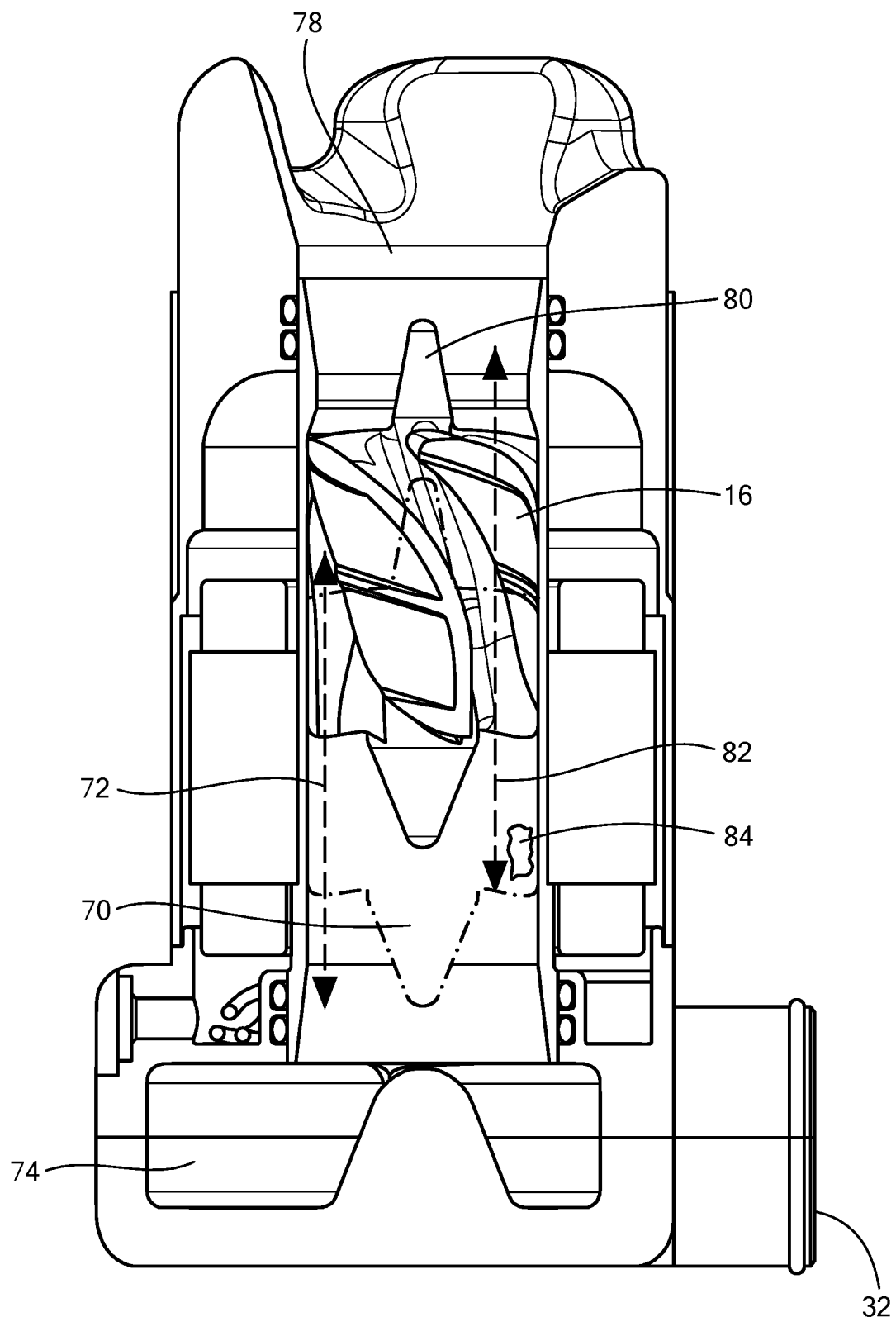
FIG. 6 is a cross-sectional view that illustrates the blood pump of FIG. 1 including the impeller being in second axial position relative to the pump housing.
Figure 7:
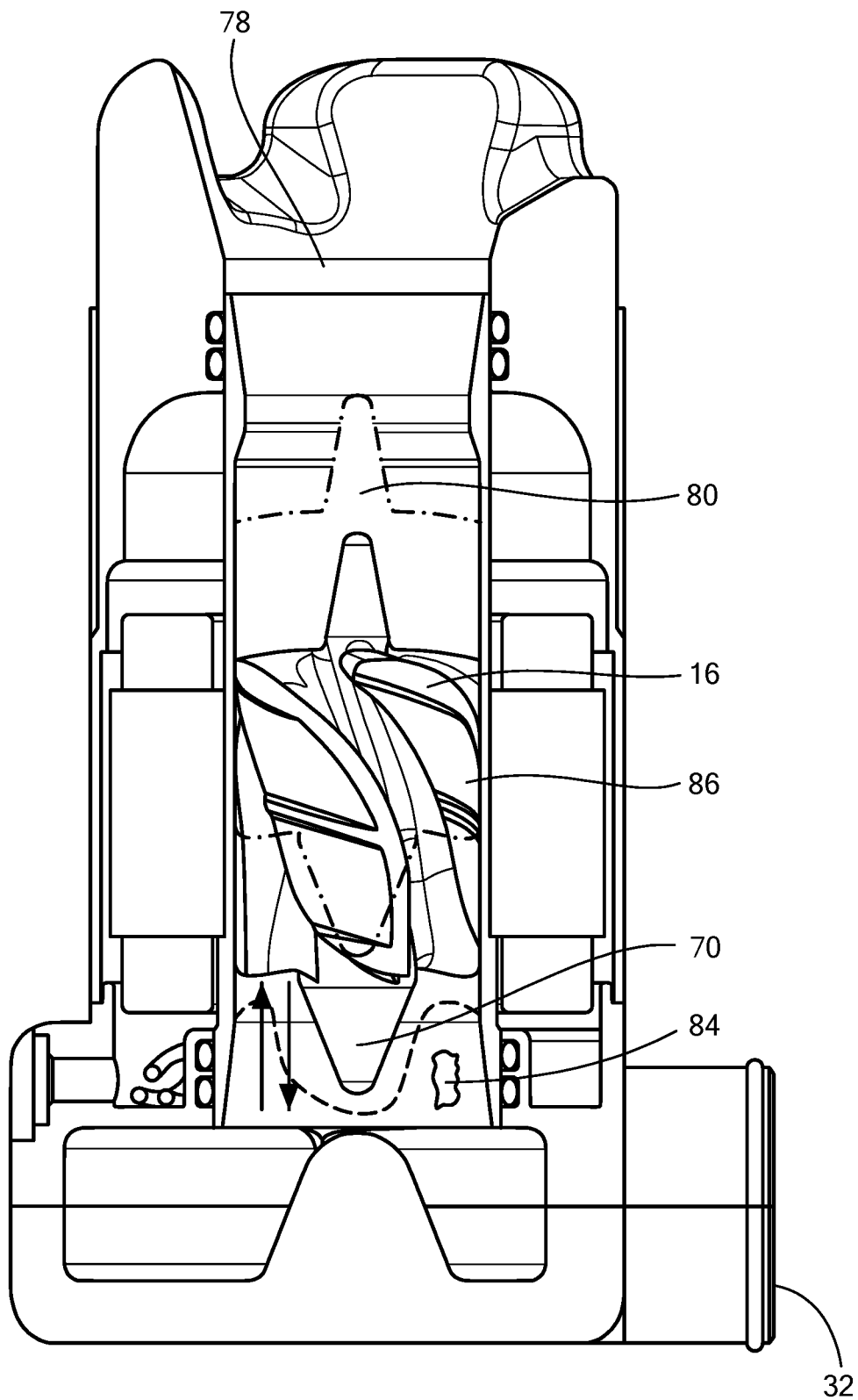
FIG. 7 is a cross-sectional view that illustrates the blood pump of FIG. 1 including the impeller being in a third axial position relative to the pump housing.

FIGS. 6-7 are cross-sectional views that illustrate the blood pump of FIG. 1 taken along section A-A of FIG. 4. With reference to FIGS. 3 and 6-7, in step 64, the method includes the control circuit 36 executing a control command when the impeller 16 is within the normal operating region 72 to temporarily displace the impeller 16 from the first axial position 70 to a second axial position 80 a distance away from the first axial position 70 using a vector control method. The control command may be executed using the controller 56 or another system or device operable to communicate with the motor 34. In one configuration, the vector control method is the three-phase sensorless field-oriented control method described above including the set of three stator windings and the set of three alternating currents. In other configurations, the vector control method may be an alternative variable-frequency drive (VFD) control method.

The second axial position 80 includes the impeller 16 being displaced in a direction toward the inlet 78 within a displacement region 82 which generally includes the impeller 16 being closer in proximity to the inlet 78 than the outlet channel 74. In other words, the second axial position 80 is upstream from the first axial position 70. The distance between the first axial position 70 and the second axial position 80 may be percentage based, such as through the use of an algorithm taking into account the first axial position 70 and the dimensions of the blood pump 10 along the pump axis A. For example, the distance may be a percent of the height of the inlet cannula 14 relative to the first axial position 70. In other configurations, the distance may be based upon one or more designated points along the pump axis A as a function of time, for example, a sine waveform pattern, predetermined increments, etc. The control command may be executed upon detecting a foreign particle 84 present within the housing 12 proximate the impeller 16, for example, when the impeller 16 is in the first axial position 70 in the normal operating state. The foreign particle 84 being proximate the impeller 16 includes the presence of the foreign particle 84 within the inlet cannula 14. The foreign particle 84 may be a blood clot, such as thrombus, or another substance or material which may be harmful to the patient and/or which may affect rotation of the impeller 16.

Figure 8:
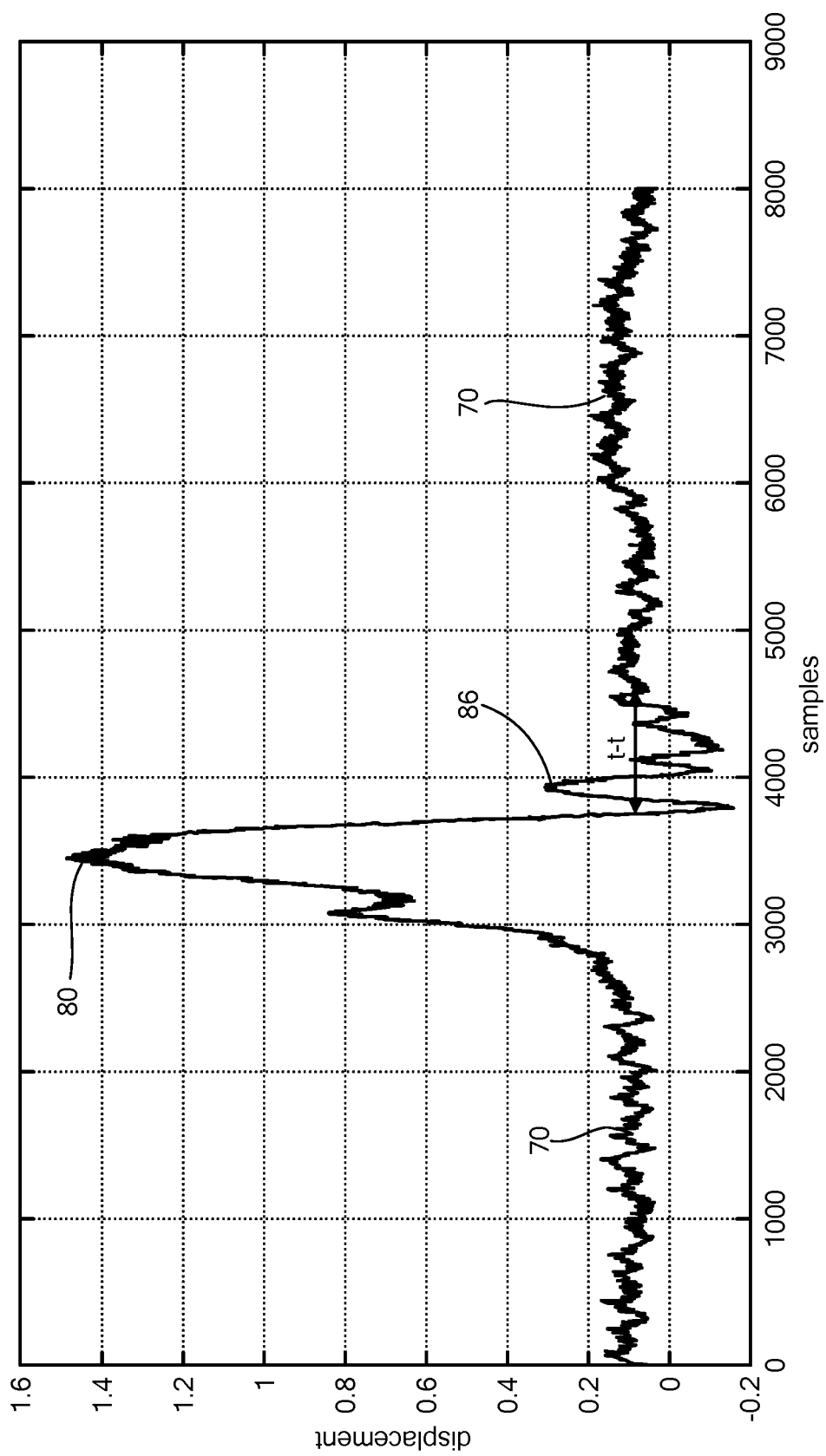
FIG. 8 is a graph that illustrates a model trajectory path of the impeller of FIG. 1 following a model implementation of the method of controlling the axial motion of the impeller.

FIG. 8 is a graph that illustrates a trajectory path of the impeller 16. With reference to FIGS. 3 and 7-8, in step 66, the method includes causing the impeller 16 to move from the second axial position 80 to a third axial position 86. Such movement from the second axial position 80 to the third axial position 86 includes the impeller 16 undergoing a positive and a negative displacement relative to the first axial position 70. The third axial position 86 includes the impeller 16 traveling in the downstream direction. The positive and a negative displacement of the impeller 16 defines an oscillating motion which may be similar to a spring, ringing, or vibratory motion configured to rinse the impeller 16 and displace the foreign particle 84 in a direction toward the outlet 32. The terms "positive and negative displacement" and "oscillating motion" may be used interchangeably herein. The oscillating motion may occur within a relatively rapid time period, such as 0.1-1.0 second, or another time period depending upon the specifics of the blood pump 10 and the vector control method. The oscillating motion may be activated when the foreign particle is detected and/or periodically, such as in sync with the patient's cardiac cycle.

In one example, the positive and a negative displacement is caused by the hydraulic and magnetic suspension system of the blood pump 10. In another example, the positive and a negative displacement may occur as a result of implementing setpoints, such as in an open loop system. Thus, the movement of the impeller 16 from the second axial position 80 to the third axial position 86 may be controlled through the vector control, whereas the oscillating motion may occur as a result of the hydraulic and magnetic suspension system. In one example, the movement from the second axial position 80 to the third axial position 86 may be along a trajectory path at least partially defined by an axial stiffness of the blood pump 10 provided by the magnetic interaction between the stator 26 and the impeller 16. Once the oscillating motion is complete, the hydraulic and magnetic suspension system may be configured to cause the impeller 16 to return to the first axial position 70 in the normal operating state.

As mentioned above, FIG. 8 illustrates an exemplary graph of a trajectory path of the impeller 16 following a model implementation of the method of controlling the axial motion of the impeller 16. The graph is provided for illustrative and exemplary purposes only as other distances and settings may be achieved through the axial motion control. Although FIG. 8 includes a depiction of between 950-1,050 samples taking place between 0.20-0.30 seconds, the number of samples taken and the time duration may vary.

The first axial position 70 may be a relative zero-reference point. The control command may be executed to displace the impeller 16 to the second axial position 80, which may be, for example, between 1.0-1.5 mm from the first axial position 70, such as toward the inlet 78. Thereafter, the impeller 16 may be displaced from the second axial position 80 to the third axial position 86 towards the outlet 32, with the third axial position 86 depicted as being between 0.4 to −0.2 mm on the graph. In the third axial position 86 the hydraulic and magnetic suspension system may cause the impeller 16 to undergo the positive and a negative displacement relative to the first axial position 70.

The time period of the positive and the negative displacement is generally designated using the "t-t" interval and may include a radial component in which the impeller 16 moves radially within the housing 12 as designated by the graph showing left to right movement. In one example, the t-t interval is between 0.15-0.25 seconds; however, other time periods are contemplated. Following the t-t interval, the impeller 16 may return to the first axial position 70.

Figure 9:
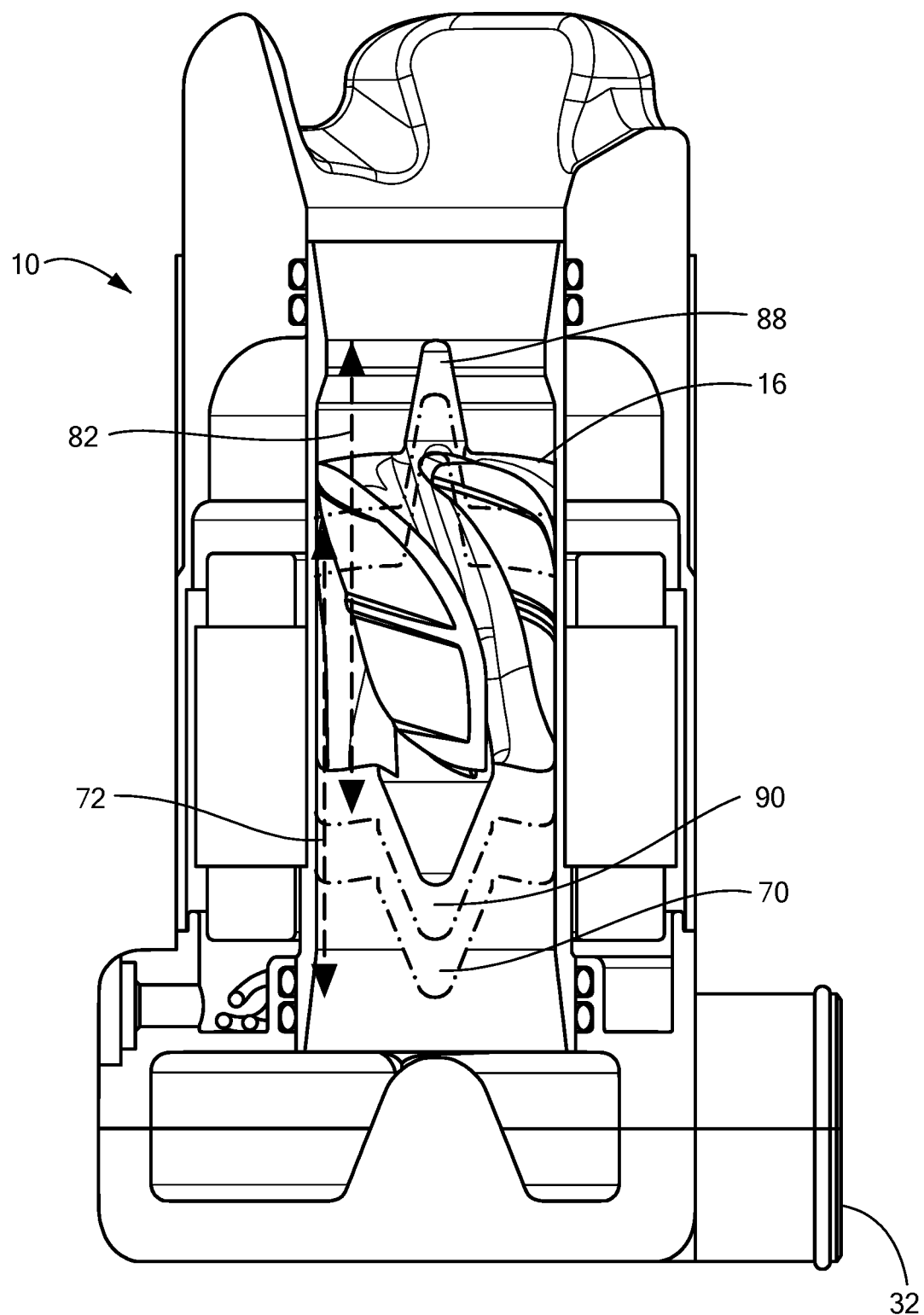
FIG. 9 is a cross-sectional view that illustrates the blood pump of FIG. 1 including the impeller being in the first axial position of FIG. 5, a fourth axial position, and a fifth axial position relative to the pump housing.

FIG. 9 is a cross-sectional view that illustrates the blood pump 10 taken along section A-A of FIG. 4 and the impeller 16 being in the first axial position, a fourth axial position, and a fifth axial position relative to the pump housing 12. For example, the method may include executing a second control command to control displacement of the impeller 16 similar to the manner described above with respect to the control command. The second control command temporarily displaces the impeller 16 from the first axial position 70 to a fourth axial position 88 a distance away from the first axial position 70 using the vector control method described above. The distance between the first axial position 70 and the fourth axial position 88 may be vary depending upon the parameters of the vector control. The fourth axial position 88 may be within the displacement region 82 yet may differ from the second axial position 80.

Similar to the movement of the impeller 16 from the second axial position 80 to the third axial position 86, the vector control may cause the impeller 16 to move in the downstream direction from the fourth axial position 88 to a fifth axial position 90 which may differ from the third axial position 86 described above. In the fifth axial position 90, the hydraulic and magnetic suspension system may cause the impeller 16 to undergo the positive and the negative displacement relative to the first axial position 70 to rinse the impeller 16, thereby dislodging one or more foreign particles 84 which may be present within the blood pump 10. The duration of the positive and the negative displacement may differ from that which occurred following the preceding control command. The second control command may be performed within a select time period following the control command, such as seconds or minutes, to perform a routine impeller rinse or dislodge one or more of the foreign particles 84 which may vary in size. For example, the impeller 16 may benefit from a second rinse to dislodge a relatively large foreign particle 84 from within the blood pump 10. The method is not limited to two control commands as three or more control commands may be implemented. The method ends at step 68.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of controlling a blood pump, the method comprising:
   executing a control command to temporarily displace an impeller of the blood pump within a pump housing from a first axial position relative to the pump housing to a second axial position a distance away from the first axial position using a vector control method; and
   causing the impeller to move from the second axial position to a third axial position, the third axial position including a positive and a negative displacement of the impeller relative to the first axial position, the positive and the negative displacement of the impeller defines an oscillating motion.

2. The method according to claim 1, further comprising dislodging a foreign particle from the pump housing when the foreign particle is proximate the impeller and the impeller is in the third axial position.

3. The method according to claim 1, wherein a hydraulic and magnetic suspension system of the blood pump causes the positive and a negative displacement of the impeller.

4. The method according to claim 1, wherein the distance of the first axial position relative to the pump housing corresponds to a thrust produced by the impeller.

5. The method according to claim 1, further comprising controlling a movement of the impeller from the second axial position to the third axial position.

6. The method according to claim 1, further comprising executing a second control command to temporarily displace the impeller from the first axial position to a fourth axial position a distance away from the first axial position using the vector control method and causing the impeller to move from the fourth axial position to a fifth axial position, the fifth axial position including a positive and a negative displacement of the impeller relative to the first axial position.

7. The method according to claim 1, wherein the vector control method is a three-phase sensorless field-oriented control method including a set of three stator windings and a set of three alternating currents.

8. The method according to claim 1, further comprising executing the control command when the first axial position of the impeller is within a normal operating region, and the normal operating region is closer in proximity to an outlet of the pump housing than an inlet of the pump housing.

9. The method according to claim 8, wherein the second axial position is within a displacement region, and the displacement region is in a direction toward the inlet of the pump housing.

10. A method of controlling a blood pump, the method comprising:
    detecting a presence of a foreign particle within a pump housing proximate an impeller of the blood pump when the impeller is in a first axial position relative to the pump housing, the first axial position including the impeller being closer in proximity to an outlet of the blood pump than an inlet of the blood pump;
    executing a control command to temporarily displace the impeller from the first axial position to a second axial position using a vector control method, the second axial position being in a direction toward the inlet of the blood pump; and
    causing the impeller to move from the second axial position to a third axial position, the third axial position including a positive and a negative displacement of the impeller relative to the first axial position, the positive and the negative displacement of the impeller defines an oscillating motion configured to displace the foreign particle in a direction toward an outlet of the pump housing.

11. The method according to claim 10, wherein a hydraulic and magnetic suspension system of the blood pump causes the positive and a negative displacement of the impeller and the displacement of the impeller from the first axial position relative to the pump housing corresponds to a thrust produced by the impeller.

12. The method according to claim 10, further comprising executing a second control command within a select time period following the control command to temporarily displace the impeller from the first axial position to a fourth axial position a distance away from the first axial position using the vector control method.

13. The method according to claim 12, further comprising causing the impeller to move from the fourth axial position to a fifth axial position, the fifth axial position including a positive and a negative displacement of the impeller relative to the first axial position.

14. The method according to claim 10, wherein the displacement of the impeller from the first axial position to the second axial position includes the impeller traveling along a trajectory path at least partially defined by an axial stiffness of the blood pump.

15. A system for controlling a blood pump comprising:
a control circuit for communicating with the blood pump, the control circuit including control circuitry configured to:
execute a control command to temporarily displace an impeller of the blood pump within a pump housing from a first axial position relative to the pump housing to a second axial position a distance away from the first axial position using a vector control method; and
cause the impeller to move from the second axial position to a third axial position, the third axial position including a positive and a negative displacement of the impeller relative to the first axial position, the positive and the negative displacement of the impeller defines an oscillating motion.

16. The system according to claim 15, wherein the distance of the first axial position relative to the pump housing corresponds to a thrust produced by the impeller.

17. The system according to claim 15, wherein the vector control method is a three-phase sensorless field-oriented control method including a set of three stator windings and a set of three alternating currents.

* * * * *